(12) United States Patent
Knochenmuss

(10) Patent No.: US 10,184,920 B2
(45) Date of Patent: Jan. 22, 2019

(54) METHOD AND APPARATUS FOR DETERMINING A CHROMATOGRAM

(71) Applicant: TOFWERK AG, Thun (CH)

(72) Inventor: Richard Knochenmuss, Seftigen (CH)

(73) Assignee: TOFWERK AG, Thun (CH)

( * ) Notice: Subject to any disclaimer, the term of this patent is extended or adjusted under 35 U.S.C. 154(b) by 105 days.

(21) Appl. No.: 15/123,558

(22) PCT Filed: Mar. 4, 2014

(86) PCT No.: PCT/CH2014/000027
§ 371 (c)(1),
(2) Date: Sep. 2, 2016

(87) PCT Pub. No.: WO2015/131293
PCT Pub. Date: Sep. 11, 2015

(65) Prior Publication Data
US 2017/0074839 A1  Mar. 16, 2017

(51) Int. Cl.
*G06F 11/30* (2006.01)
*G01N 30/46* (2006.01)
(Continued)

(52) U.S. Cl.
CPC .......... *G01N 30/466* (2013.01); *G01N 30/72* (2013.01); *G01N 30/86* (2013.01);
(Continued)

(58) Field of Classification Search
CPC .................................................. G01N 30/466
See application file for complete search history.

(56) References Cited

U.S. PATENT DOCUMENTS

| 5,205,845 A | 4/1993 | Sacks et al. |
| 5,492,838 A | 2/1996 | Pawliszyn |

(Continued)

FOREIGN PATENT DOCUMENTS

| DE | 10 2005 050 114 A1 | 4/2007 |
| WO | WO 00/46929 A1 | 8/2000 |
| WO | WO 00/45929 | * 10/2000 |

OTHER PUBLICATIONS

Chinese Office Action dated Jul. 21, 2017 in corresponding Chinese Application No. 201480078554.1 with an English Translation.
(Continued)

*Primary Examiner* — Phuong Huynh
(74) *Attorney, Agent, or Firm* — Birch, Stewart, Kolasch & Birch, LLP

(57) ABSTRACT

The invention relates to a method and an apparatus for determining a chromatogram. The method includes a first step where a sample is inserted in two separation columns (2.1, 2.2, 2.3), wherein for each separation column (2.1, 2.2, 2.3), a corresponding part of the sample is inserted in the respective separation column (2.1, 2.2, 2.3) with a corresponding insertion device (3.1, 3.2, 3.3) which is controlled by a corresponding modulation function for generating a corresponding modulated part of the sample in the respective separation column (2.1, 2.2, 2.3), wherein the modulation functions with which the parts of the sample are modulated in the separation columns (2.1, 2.2, 2.3) differ from each other. Furthermore, the method includes a second step where each modulated part of the sample is guided through the respective separation column (2.1, 2.2, 2.3), a third step where a signal of each modulated part of the sample is measured with a same detector (4) after having passed the respective separation column (2.1, 2.2, 2.3), and a fourth step where for each separation column (2.1, 2.2, 2.3), a correlation of the signal and the modulation function
(Continued)

with which the corresponding part of the sample is modulated in the respective separation column (2.1, 2.2, 2.3) is calculated in order to determine the chromatogram of the respective separation column (2.1, 2.2, 2.3).

16 Claims, 3 Drawing Sheets

(51) Int. Cl.
*G01N 30/72* (2006.01)
*G01N 30/86* (2006.01)
G01N 30/62 (2006.01)
G01N 30/02 (2006.01)

(52) U.S. Cl.
CPC ... *G01N 30/8658* (2013.01); *G01N 2030/025* (2013.01); *G01N 2030/027* (2013.01); *G01N 2030/623* (2013.01); *G01N 2030/628* (2013.01); *G01N 2030/862* (2013.01)

(56) References Cited

U.S. PATENT DOCUMENTS

| | | |
|---|---|---|
| 2002/0084222 A1 | 7/2002 | Brann |
| 2006/0163133 A1 | 7/2006 | Brann |
| 2008/0295617 A1 | 12/2008 | Trapp |
| 2009/0250607 A1 | 10/2009 | Staats et al. |

OTHER PUBLICATIONS

Smit, "Correlation chromatography", Trends in Analytical Chemistry, vol. 2, No. 1, 1983, pp. 1-7.

\* cited by examiner

METHOD AND APPARATUS FOR DETERMINING A CHROMATOGRAM

TECHNICAL FIELD

The invention relates to a method and an apparatus for determining a chromatogram with more than one separation column connected to a shared detector.

BACKGROUND ART

Methods and apparatus' pertaining to the technical field initially mentioned are known. U.S. Pat. No. 5,205,845 of the Regents of the University of Michigan for example describes an apparatus and a method for gas chromatography with more than one separation column having different separation characteristics. The sample is injected with an injection sequence into these columns and the analyte eluted from the columns is measured with a shared detector to obtain a composite of the outputs from the columns. This composite is a single chromatogram which provides a good resolution of all components of interest because the characteristics of the columns and the injection sequence are chosen so that significant peaks can be superimposed relative to the output of the other columns. In order to achieve this, the portions of a single column chromatogram which are ordinarily free of peaks are used to insert peaks from another column related to specific compounds of interest.

Similarly, US 2009/0250607 A1 of Phoenix S&T Inc. discloses an apparatus and a method for liquid chromatography with more than one liquid chromatography column and a mass spectrometer as shared detector. In this case, the number of columns and spray devices employed is a number at which a cyclic Hadamard simplex matrix exists. To the end of each column, a separate sample spraying device is connected. These spraying devices are positioned aiming at the mass spectrometer inlet and spray when a high voltage is applied. When operated, the high voltage is applied in different Hadamard sequences to the different spraying devices such that each spray device sprays only during the "on" state of the respective Hadamard sequence when the high voltage is applied and stops spraying during the "off" state of the respective sequence. During one peak in the chromatogram of a column, an entire Hadamard-Sequence is applied to the spray device of the respective column. In the signal measured by the mass spectrometer, the column from which the signal originates can be identified because of a missing signal at a particular time in the Hadamard sequence.

The disadvantage of the apparatus' and methods described in U.S. Pat. No. 5,205,845 and US 2009/0250607 A1 is that a lot of time is required for obtaining a full chromatogram which comprises the information of the chromatograms of the individual separation columns.

Another apparatus and method where this disadvantage is at least partially overcome is described in U.S. Pat. No. 5,492,838 of Pawliszyn. In this example, the substances are extracted from a liquid phase in a gas chromatography column by single or multiple cooling or heating pulses. These pulses may be of random sequence. After having measured the extracted substances with a detector, the obtained signal is deconvoluted with a cross-correlation, a Fourier transform or a Hadamard transform in order to obtain a continuous analysis of the extracted substances. However, this example has the disadvantage that a measurement can only be obtained for one column at a time.

SUMMARY OF THE INVENTION

It is the object of the invention to create a method and an apparatus pertaining to the technical field initially mentioned that enables obtaining a full chromatogram comprising the information of the chromatograms of more than one separation column more quickly while maintaining the signal to noise ratio in the chromatograms.

The solution of the invention is specified by the features of the independent claims.

According to the invention, the method for determining a chromatogram includes a first step where a sample is inserted in two separation columns, wherein for each separation column, a corresponding part of the sample is inserted in the respective separation column with a corresponding insertion device which is controlled by a corresponding modulation function for generating a corresponding modulated part of the sample in the respective separation column, wherein the modulation functions with which the parts of the sample are modulated in the separation columns differ from each other. Furthermore, the method includes a second step where each modulated part of the sample is guided through the respective separation column, a third step where a signal of each modulated part of the sample is measured with a same detector after having passed the respective separation column, and a fourth step where for each separation column, a correlation of the signal and the modulation function with which the corresponding part of the sample is modulated in the respective separation column is calculated in order to determine the chromatogram of the respective separation column.

According to the invention, an apparatus for determining a chromatogram according to the method comprises at least two separation columns. Furthermore, the apparatus comprises for each separation column an inserting device for inserting a part of a sample into the respective separation column, the inserting devices each being controlled by a corresponding modulation function for generating a corresponding modulated part of the sample in the respective separation column, wherein the modulation functions with which the parts of the sample are modulatable in the separation columns differ from each other. Additionally, the apparatus comprises a detector for measuring a signal of the modulated parts of the sample after having passed the respective separation column, and a calculation unit for calculating for each separation column the correlation of the signal with the modulation function with which the part of the sample which is inserted into the respective separation column is modulated in order to determine the chromatograms of the separation columns.

With this solution, it is sufficient to employ one detector which can measure a time dependent signal of the sample arriving at the detector. Since the output of the different separation columns is fed to this detector, the signal measured by the detector comprises a superposition of the signals from the modulated parts of the sample after they have passed their respective separation column. Calculating the correlation of the signal measured by the detector with each of the modulation functions used for modulating the parts of the sample provides the chromatogram of each separation column because in each separation column, the corresponding part of the sample is modulated with another modulation function when being inserted in the respective separation column. Therefore, the full chromatogram can be obtained by calculating for each separation column the correlation which comprises the chromatogram of the respective separation column. With this procedure, it is possible to connect permanently all separation columns to the detector instead of connecting the separation columns in a sequence of one separation column after the other separation column to the detector in a way that only one of the separation columns is connected to the detector at a given time. When being permanently connected to all separation columns, the detector permanently measures sample coming from all separation columns. Therefore, the signal to noise ratio for the chromatograms obtained for the individual separation columns is improved as compared to the case where only one of the separation columns is connected to the detector at a given time. Consequently, the solution of the invention has the advantage that a full chromatogram of more than one separation column can be obtained with one detector in a same time with an improved signal to noise ratio as compared to the case where only one separation column is connected to the detector at a given time. Or, if maintaining the signal to noise ratio, a full chromatogram of more than one separation column can be obtained with one detector more quickly than in the case where only one of the separation columns is connected to the detector at a given time.

It is to be noted that in the present context, the term "sample" is used in two different ways. In the first way, it is used for one single sample which is to be investigated. In this case, this sample is divided into parts which are each fed to one of the insertion devices. Consequently, for each separation column a chromatogram of the same sample is obtained. In the second way, the term "sample" subsumes two or more different samples which are to be investigated. In this case, these different samples are considered as "parts of the sample" which are each fed to one of the insertion devices. Consequently, the chromatograms of the separation columns are obtained for the respective samples that are considered as "parts of the sample" and which are subsumed to the "sample" which is to be investigated.

Preferably, in the first step of the method, the sample is inserted in three, four, five or more separation columns, wherein for each separation column, a corresponding part of the sample is inserted in the respective separation column with a corresponding insertion device which is controlled by a corresponding modulation function for generating a corresponding modulated part of the sample in the respective separation column, wherein the modulation functions with which the parts of the sample are modulated in the separation columns differ from each other. Furthermore, in the second step, each modulated part of the sample is preferably guided through the respective separation column, wherein in the third step, the signal of each modulated part of the sample is preferably measured with the same detector after having passed the respective separation column, and wherein in the fourth step, for each separation column, a correlation of the signal and the modulation function with which the corresponding part of the sample is modulated in the respective separation column is preferably calculated in order to determine the chromatogram of the respective separation column. This has the advantage that a full chromatogram of more than two separation columns can be obtained.

Alternatively, the sample may be inserted in only two separation columns in the first step of the method. This alternative is advantageous in case the chromatograms of only two different separation columns are required.

In order to execute the method, the apparatus for determining a chromatogram according to the method advantageously comprises at least the same number of separation columns as the sample is inserted in the first step of the method. Thus, the apparatus preferably comprises two separation columns if the sample is inserted in two separation columns in the first step of the method. Similarly, the apparatus preferably comprises three, four, five or more separation columns if the sample is inserted in the respective number of separation columns in the first step of the method. But of course, the apparatus may comprise more separation columns than the number of separation columns the sample is inserted in the first step of the method.

Independent of the number of separation columns comprised by the apparatus, the apparatus advantageously comprises for each separation column an inserting device for inserting a part of the sample into the respective separation column, the inserting devices each being controlled by a corresponding modulation function for generating a corresponding modulated part of the sample in the respective separation column, wherein the modulation functions with which the parts of the sample are modulatable in the separation columns differ from each other.

Preferably, in the first step of the method, there is an overlapping time interval where all parts of the sample are inserted simultaneously in their respective separation column modulated with their respective modulation function. This has the advantage that the time required for taking a measurement for determining a full chromatogram with the chromatograms of all separation columns is minimised.

This preferred variant of the method may be employed, too, if in the first step, the sample is inserted in more than two separation columns. However, in case the sample is inserted in more than two separation columns, there is a further preferred variant where in the first step of the method, there is a partial overlapping time interval where at least two of the parts of the sample are inserted simultaneously in their respective separation column modulated with their respective modulation function. This has the advantage that the time required for taking a measurement is minimised or at least reduced.

Alternatively, there may be no such overlapping time interval or partial overlapping time interval.

In a further preferred variant of the method, the insertion of the parts of the sample into their respective separation columns is begun at a same time in the first step of the method. This has the advantage that there is no time offset to be considered when determining the chromatograms of the individual separation columns. Consequently, this has the advantage that the risk of unnoticed systematic errors in the obtained chromatograms is reduced.

Alternatively, the insertion of the parts of the sample into their respective separation columns may be begun at different times. Such an alternative may for example be advantageous if one or more of the separation columns is considerably slower passed by the sample than the other one or more separation columns.

In one preferred variant, the autocorrelation of at least one of the modulation functions is a function with one single peak and low sidebands. In this case, the highest point in the sidebands has preferably a height as compared to the lowest point in the sidebands which is less than five times, preferably less than ten times, and even more preferably less than twenty times the height of the single peak in the autocorrelation, wherein the height of the single peak is the difference between the single peak's maximum intensity and the average intensity of the sidebands. This has the advantage that for the separation column in which the sample is inserted with the modulation function with the autocorrelation with the single peak and the low sidebands, a more precise determination of the chromatogram is achieved. In particular, calculating the correlation of the respective modulation function with the signal measured with the detector shifts only a marginal part of the signal originating from the part of the sample which has passed the respective separation column and which has been properly modulated with the respective modulation function to an incorrect position in the correlation.

In a second preferred variant, an autocorrelation of at least one of the modulation functions is a two-valued function. This has the advantage that for the separation column in which the sample is inserted with the modulation function with the two-valued autocorrelation, a more precise determination of the chromatogram is achieved. In particular, calculating the correlation of the respective modulation function with the signal measured with the detector does not shift signal originating from the part of the sample which has passed the respective separation column and which has been properly modulated with the respective modulation function to an incorrect position in the correlation. Thus, the signal to background ratio in the correlation is optimised.

In a third preferred variant, the autocorrelation of each of the modulation functions is a function with one peak and low sidebands. In this case, the highest point in the sidebands has preferably a height as compared to the lowest point in the sidebands which is less than five times, preferably less than ten times, and even more preferably less than twenty times the height of the single peaks in the autocorrelations, wherein the height of the single peaks is the difference between the single peaks' maximum intensity and the average intensity of the respective autocorrelation's sidebands. This has the advantage that a more precise determination of the chromatograms of the individual separation columns is achieved. In particular, calculating the correlation of any of the modulation functions with the signal measured with the detector shifts only a marginal part of the signal originating from the part of the sample which has passed the respective separation column and which has been properly modulated with the respective modulation function to an incorrect position in the correlation.

In a fourth preferred variant, the autocorrelation of each of the modulation functions is a two-valued function. This has the advantage that a more precise determination of the chromatograms of the individual separation columns is achieved. In particular, calculating the correlation of any of the modulation functions with the signal measured with the detector does not shift signal originating from the part of the sample which has passed the separation column where the sample is inserted modulated with the respective modulation function and which has been properly modulated with the respective modulation function to an incorrect position in the correlation.

Advantageously, the modulation functions have a same length. This has the advantage that the signal measured by the detector can be optimally used for determining the chromatograms of the individual separation columns.

Alternatively, the modulation functions may have different lengths. Such an alternative may for example be advantageous if there are considerable differences in the time the sample takes to pass the different separation columns.

If the modulation functions have a same length, the length of the modulation functions is advantageously at least the number of separation columns times the time the sample requires to pass the separation column that is passed the slowest by the sample. This has the advantage that a good signal to noise ratio in the chromatograms of the individual separation columns is obtained.

Alternatively, the modulation functions may be shorter. Such an alternative has the advantage that a measurement may be performed in shorter time.

In one preferred variant, a cross-correlation of two modulation functions chosen from the modulation functions has a nearly constant value over its entire length. This has the advantage that for the two separation columns in which the sample is inserted with one of these two modulation functions, a more precise determination of the chromatogram is achieved. In particular, calculating the correlation of one of these two modulation functions with the signal measured with the detector moves only a marginal part of the signal originating from the part of the sample which has been properly modulated with the other one of the two modulation functions and which has passed the corresponding separation column into the calculated correlation.

In a second preferred variant, the cross-correlation of each pair of two modulation functions chosen from the modulation functions has a nearly constant value over its entire length. This has the advantage that a more precise determination of the chromatograms of the individual separation columns is achieved. In particular, calculating the correlation of one of the modulation functions with the signal measured with the detector moves only a marginal part of the signal originating from a part of the sample which has been properly modulated with another one of the modulation functions and which has passed the corresponding separation column into the calculated correlation.

In a third preferred variant, the cross-correlation of two modulation functions chosen from the modulation functions is a function with a single peak at a peak position.

In a fourth preferred variant, the cross-correlation of each pair of two modulation functions chosen from the modulation functions is a function with a single peak at a peak position. However, it is not required that the cross-correlations of all possible pairs of two modulation functions chosen from the modulation functions are functions with a single peak at a peak position. It is as well possible that the cross-correlations of only some of the pairs of two modulation functions chosen from the modulation functions are functions with a single peak at a peak position. In case there are two or more pairs of modulation functions with a cross-correlation being a function with a single peak at a peak position, the single peaks in the different cross-correlations may be located at different peak positions. Independent of the number of such pairs of modulation functions and independent of the peak positions of the single peaks in the different cross-correlations, there exist many pairs of modulation functions with a cross-correlation with a single peak, the modulation functions having at the same time an autocorrelation with advantageous, above mentioned properties. Thus, a set of suitable modulation functions can readily be put together for executing the method and for employing in the apparatus, respectively.

Due to the single peak in the cross-correlation, the correlation calculated from the signal measured by the detector and one of the respective two modulation functions comprises the peaks from the chromatogram belonging to the separation column where the sample is inserted modulated with the other one of the two respective separation functions. These peaks originating from the other chromatogram can be identified in the correlation if their approximate positions in the other chromatogram and the position of the single peak in the cross-correlation of the respective two modulation functions are known. Thus, these peaks originating from this other chromatogram can be identified and subtracted from the correlation in order to obtain the desired chromatogram.

In a first advantageous variation of the third or fourth preferred variant, the cross-correlation of the respective two modulation functions chosen from the modulation functions is a function with a single peak at a peak position and with low sidebands. In this variation, the highest point in the sidebands has preferably a height as compared to the lowest point in the sidebands which is less than five times, preferably less than ten times, and even more preferably less than twenty times the height of the single peak in the cross-correlation, wherein the height of the single peak is the difference between the single peak's maximum intensity and the average intensity of the sidebands. This has the advantage that for the two separation columns in which the sample is inserted with one of the respective two modulation functions, a more precise determination of the corresponding chromatogram can be achieved. In order to obtain the chromatogram of a first one of these two separation columns, the correlation of the signal measured with the detector and the modulation function with which the corresponding part of the sample is inserted in the first one of the two separation columns is calculated. Subsequently, the peaks in the correlation which originate from the second chromatogram belonging to the second one of the two separation columns are subtracted. The result is a chromatogram which comprises only a marginal part of incorrect information originating from a part of the sample which has passed the second separation column and which has been properly modulated with the corresponding second modulation function. Of course, the chromatogram of the second one of the two separation columns can be obtained in the same manner by subtracting from the correlation between the signal and second modulation function the peaks originating from the first chromatogram.

In a second advantageous variation of the third or fourth preferred variant, the cross-correlation of the respective two modulation functions chosen from the modulation functions is a function with a single peak at a peak position and with constant side bands. This has the advantage that for the two separation columns in which the sample is inserted with one of the respective two modulation functions, a more precise determination of the chromatogram can be achieved. In order to obtain the chromatogram of a first one of these two separation columns, the correlation of the signal measured with the detector and the modulation function with which the corresponding part of the sample is inserted in the first one of the two separation columns is calculated. Subsequently, the peaks in the correlation which originate from the second chromatogram belonging to the second one of the two separation columns are subtracted. The result is a chromatogram which does not comprise any incorrect information originating from a part of the sample which has passed the second separation column and which has been properly modulated with the corresponding second modulation function. Of course, the chromatogram of the second one of the two separation columns can be obtained in the same manner by subtracting from the correlation between the signal and the second modulation function the peaks originating from the first chromatogram.

In a third advantageous variation of the third or fourth preferred variant, the cross-correlation of the respective two modulation functions chosen from the modulation functions is a two-valued function with a single peak at a peak position. This has the same advantage as the second advantageous variation where the cross-correlation is a function with a single peak at a peak position and with constant sidebands. However, the third advantageous variation has the additional advantage that it is easier to subtract the peaks originating from the other chromatogram from the calculated correlation in order to obtain the desired chromatogram. The reason is that the peaks in the correlation which originate from the other chromatogram are very narrow because of the single peak in the cross-correlation is very sharp. Therefore, there is a smaller probability that in the correlation, they partially or fully overlap with peaks of the desired chromatogram.

As an alternative to the five above mentioned preferred variants with their respective variations, the cross-correlation of one or more than one of the possible pairs of two modulation functions chosen from the modulation functions is a function with no peak or with more than one peak.

If the cross-correlation of any two modulation functions chosen from the modulation functions comprises a single peak at a peak position, in a first preferred variant, the peak position of this single peak is located in the cross-correlation in a region with a length of 1%, 2%, 5%, 10% or 20% of the cross-correlation's length, the region's centre being located at a distance from an end of the cross-correlation, the distance being an integer multiplied with the length of the cross-correlation divided by the number of employed separation columns. In order that the region is located within the cross-correlation, the integer may have any value from zero up to the number of employed separation columns. Independent of the integer's value, this has the advantage that the position of the single peak in the respective cross-correlation is sufficient precisely known. Consequently, if the correlation between a first one of the respective two modulation functions and the signal measured with the detector is calculated, the peaks in this correlation which originate from the second chromatogram belonging to the second one of the two separation columns where the part of the sample is inserted modulated with the second one of the respective two modulation functions can easily be identified.

In a second preferred variant, the peak position is located in the cross-correlation at a distance from an end of the cross-correlation, the distance being an integer multiplied with the length of the cross-correlation divided by the number of employed separation columns. In order that the region is located within the cross-correlation, the integer may have any value from zero up to the number of employed separation columns. Independent of the integer's value, this has the advantage that the position of the single peak in the respective cross-correlation is precisely known. Consequently, if the correlation between a first one of the respective two modulation functions and the signal measured with the detector is calculated, the peaks in this correlation which originate from the second chromatogram belonging to the second one of the two separation columns where the part of the sample is inserted modulated with the second one of the respective two modulation functions can even more easily be identified.

In either of these two preferred variants, preferably the integer's value is larger than zero and less than the number of employed separation columns while the length of the modulation functions is at least the number of separation columns times the time the sample requires to pass the separation column which is passed the slowest by the sample. This has the advantage that it is simpler to determine the chromatogram from the correlation calculated from the signal measured with the detector and a first one of the respective two modulation functions. In this case, the peaks originating from the second chromatogram belonging to the second separation column, where the second part of the sample modulated with the second one of the respective two separation columns is inserted, are located at a position in the correlation which is further back than the length of the correlation divided by the number of employed separation columns. At the same time, the peaks in the correlation originating from the signal of the first part of the sample which is modulated with the first one of the respective two modulation functions are located in the correlation in a region which starts at the beginning of the correlation and which has a length corresponding the correlation divided by the number of employed separation columns. Thus, the first chromatogram of the first separation column corresponds to this region of the calculated correlation. Since the peaks from the second chromatogram are located further back in the correlation, there is no need to subtract the peaks originating from the second chromatogram from the correlation. Even more, it is not even required to know the positions of the peaks in the second chromatogram for determining the first chromatogram from the calculated correlation. For the same reason, there is no need to subtract the peaks originating from the first chromatogram from the correlation calculated from the signal measured with the detector and the second one of the respective two modulation functions in order to determine the second chromatogram because there, the peaks from the second chromatogram are located in the region at the beginning of the correlation while the peaks from the first chromatogram are located further back in the correlation. Consequently, if all possible pairs of two modulation functions chosen from the modulation functions have such a cross-correlation, there is no need to know any of the positions of the peaks in any of the chromatograms in order to determine the full chromatogram comprising the information of the chromatograms of all employed separation columns.

In an alternative embodiment, the single peak of the cross-correlation of the respective two modulation function is located in a different region of the cross-correlation.

Advantageously, the method according to the invention is a method for determining a liquid chromatogram, and the apparatus according to the invention is an apparatus for determining a liquid chromatogram. This has the advantage that a full liquid chromatogram of more than one separation column can be obtained with one detector in a same time with an improved signal to noise ratio as compared to the case where only one separation column is connected to the detector at a given time. Or, if maintaining the signal to noise ratio, a full liquid chromatogram of more than one separation column can be obtained with one detector more quickly than in the case where only one of the separation columns is connected to the detector at a given time. In this case, the employed separation columns are advantageously liquid separation columns.

Advantageously, the method according to the invention is a method for determining a gas chromatogram, and the apparatus according to the invention is an apparatus for determining a gas chromatogram. This has the advantage that a full gas chromatogram of more than one separation column can be obtained with one detector in a same time with an improved signal to noise ratio as compared to the case where only one separation column is connected to the detector at a given time. Or, if maintaining the signal to noise ratio, a full gas chromatogram of more than one separation column can be obtained with one detector more quickly than in the case where only one of the separation columns is connected to the detector at a given time. In this case, the employed separation columns are advantageously gas separation columns.

Independent of whether the method and the apparatus are a method and an apparatus for determining a liquid chromatogram, a gas chromatogram or any other type of chromatogram, the employed detector is advantageously a mass spectrometer. This has the advantage that not only a chromatogram but also a mass spectrum of the investigated sample can be obtained.

Alternatively, the detector may be some other type of detector.

Other advantageous embodiments and combinations of features come out from the detailed description below and the totality of the claims.

BRIEF DESCRIPTION OF THE DRAWINGS

The drawings used to explain the embodiments show.

In the figures, the same components are given the same reference symbols.

PREFERRED EMBODIMENTS

Figure 1:
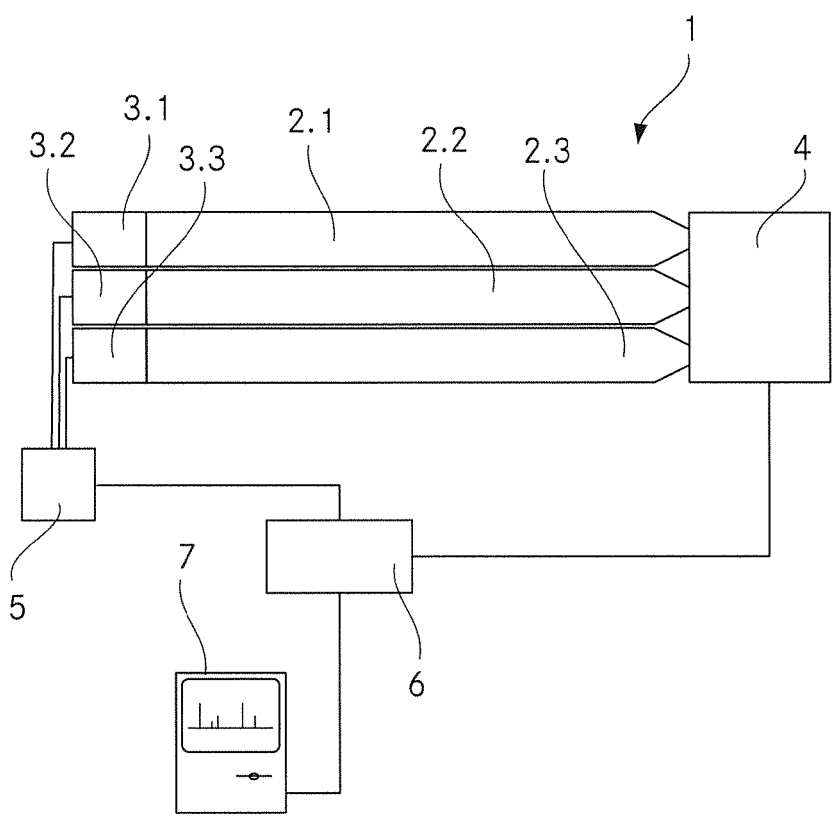
FIG. 1 a schematic view of an apparatus according to the invention for determining a chromatogram,
FIG. 2 a flowchart diagram of the method according to the invention for determining a chromatogram,
FIG. 3 one of the modulation functions employed in the apparatus and the method according to the invention together with its autocorrelation,
FIG. 4 a cross-correlation, illustrating that each pair of two modulation functions chosen from the employed modulation functions has a cross-correlation which is a two-valued function having a single peak,
FIG. 5 the chromatograms of two different separation columns, and
FIG. 6 the correlations calculated between the signals measured with the detector and the two modulation functions for obtaining the chromatograms shown in FIG. 5.

FIG. 1 shows a schematic view of an apparatus 1 according to the invention for determining a chromatogram. This apparatus 1 comprises three separation columns 2.1, 2.2, 2.3, three insertion devices 3.1, 3.2, 3.3 and a detector 4. Each of the insertion devices 3.1, 3.2, 3.3 is allocated to another one of the separation columns 2.1, 2.2. 2.3 and can insert a sample into the respective separation column 2.1, 2.2, 2.3. The detector 4 is permanently connected to all three separation columns 2.1, 2.2, 2.3 and can measure a superposition of the outputs of the three separation columns 2.1, 2.2, 2.3.

The apparatus 1 is constructed to obtain from each separation column 2.1, 2.2, 2.3 a chromatogram of a sample to be investigated. In order to obtain these chromatograms, the sample is fed to the apparatus 1 by dividing it into three parts which are each fed to one of the insertion devices 3.1, 3.2, 3.3. If the sample is a fluid, the apparatus may for example comprise a tube system which connects a sample inlet to all three separation columns 2.1, 2.2, 2.3 for feeding a part of the sample to each of the individual insertion devices 3.1, 3.2, 3.2. As an alternative, the sample may be fed directly to the insertion devices 3.1, 3.2, 3.3. In this alternative, it is possible to feed the insertion devices 3.1, 3.2, 3.3 with parts of the same sample or with completely different samples. In case the insertion devices 3.1, 3.2, 3.3 are fed with parts of the same sample, for each separation column 2.1, 2.2, 2.3 a chromatogram of the same sample is obtained. This way, a more complete analysis of the sample is obtained because the separation columns 2.1, 2.2, 2.3 have different separation properties. In the other case where the insertion devices 3.1, 3.2, 3.3 are fed with different samples, the chromatograms of the separation columns 2.1, 2.2, 2.3 are obtained for the respective samples.

In order to enable the determination of the chromatogram of an individual separation column 2.1, 2.2, 2.3 from the signal measured with the detector 4, each of the insertion devices 3.1, 3.2, 3.3 modulates the sample according to a different modulation function to form a timely modulated part of the sample in the respective separation column 2.1, 2.2, 2.3. This means that each insertion device 3.1, 3.2, 3.3 inserts the corresponding part of the sample at times when the corresponding modulation function has a value of "1", while it does not insert any sample at times when the corresponding modulation function has a value of "0". In order to control the different insertion devices 3.1, 3.2, 3.3 with the corresponding modulation function, they are connected to a control device 5. This control device 5 controls them by feeding them with the appropriate modulation functions. Furthermore, the control device 5 tunes the insertion devices 3.1, 3.2, 3.3 with respect to each other such that they all begin at a same time with inserting the respective part of the sample into the respective separation column 2.1, 2.2, 2.3 modulated with the respective modulation function.

After being inserted in the separation columns 2.1, 2.2, 2.2, the modulated parts of the sample pass through their respective separation column 2.1, 2.2, 2.3 where the constituent parts of the parts of the sample take different times to pass through the respective separation column 2.1, 2.2, 2.3 such that they become separated from each other. Thus, the output of the separation columns 2.1, 2.2, 2.3 is modulated in time with a modulation which is on the one hand caused by the modulation function with which the respective part of the sample is modulated when being inserted in the respective separation column 2.1, 2.2, 2.3 and which is on the other hand caused by the separation of the respective part of the sample into its constituent parts.

As mentioned already, the detector 4 is permanently connected to all three separation columns 2.1, 2.2, 2.3 and can measure a superposition of the outputs of the three separation columns 2.1, 2.2, 2.3. When performing a measurement, the detector 4 collects time dependent data such that the measured signal is a time dependent intensity.

However, the detector 4 may at the same time collect further data. For example, the detector 4 may be a mass spectrometer which registers the amount of sample arriving from the separation columns 2.1, 2.2, 2.3 per time unit and which determines the mass spectrum of the separation columns' 2.1, 2.2, 2.3 output arriving at the detector 4 per such time unit. Nonetheless, there is no requirement that the detector 4 is such a mass spectrometer. The detector 4 may be any other kind of detector which enables a time dependent measurement of the output coming from the separation columns 2.1, 2.2, 2.3. For this reason, the term "signal measured with the detector" is used here for the time dependent signal obtained from the detector 4 which comprises information on the time dependency of the amount of output coming from the separation columns 2.1, 2.2, 2.3.

In order to obtain the chromatograms of the individual separation columns 2.1, 2.2, 2.3, the correlations are calculated between the signal measured with the detector 4 and the modulation functions with which the parts of the sample are modulated when being inserted in their corresponding separation column 2.1, 2.2, 2.3. For this reason, the control unit 5 and the detector 4 are both connected to a calculation unit 6. The control unit 5 feeds the modulation functions with which the parts of the sample are modulated when being inserted in the separation columns 2.1, 2.2, 2.3 to the calculation unit 6, while the detector 4 feeds the measured signal to the calculation unit 6. Thus, the calculation unit 6 can calculate the correlation between the signal measured by the detector 4 and the modulation functions with which the parts of the sample are modulated when they are inserted in the separation columns 2.1, 2.2, 2.3.

In FIG. 1, the calculation unit 6 is shown as being connected to a computer 7 for displaying the obtained correlations or chromatograms, respectively. However, the calculation unit 6 may be a computer like for example a personal computer. In this case, the connection to the separate computer 7 may be omitted. Similarly, it is not required to employ a separate control unit 5. The control unit 5 may be incorporated into the calculation unit 6. Consequently, the control unit 5, the calculation unit 6 and the computer 7 shown in FIG. 1 may be combined in one computer. In this case, the computer controls the insertion devices 3.1, 3.2, 3.3, calculates the correlation between the modulation functions and the signal measured with the detector 4 and enables a further processing or displaying of the obtained correlations or chromatograms, respectively.

Figure 2:
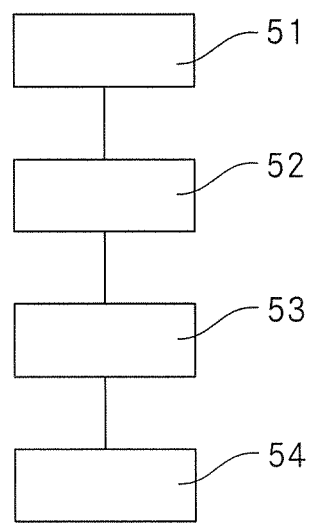

FIG. 2 shows a flowchart diagram of the method according to the invention for determining a chromatogram. This method may be executed with the apparatus 1 shown in FIG. 1.

In a first step 51 of the method, the sample is divided in a same number of parts as there are separation columns 2.1, 2.2, 2.3 from which a chromatogram should be obtained. Each of these parts is inserted into the respective separation column 2.1, 2.2, 2.3 by a corresponding insertion device 3.1, 3.2, 3.3 which modulates the respective part of the sample according to a modulation function when inserting it in the respective separation column 2.1, 2.2, 2.3. Since the different insertion devices 3.1, 3.2, 3.3 are controlled by different modulation functions, the different parts of the sample are modulated differently when being inserted in the different separation columns 2.1, 2.2, 2.3.

In a second step 52 of the method, the modulated parts of the sample are guided through their respective separation column 2.1, 2.2, 2.3.

In a third step 53 of the method, the signal of the modulated parts of the sample is measured with the detector 4 after having passed the separation columns 2.1, 2.2, 2.3. This signal measured with the detector 4 comprises a superposition of the outputs of the separation columns 2.1, 2.2, 2.3.

In a fourth step 54 of the method, for each of the separation columns 2.1, 2.2, 2.3, the correlation is calculated between the signal measured with the detector 4 and the modulation function with which the respective part of the sample has been modulated when being inserted in the respective separation column 2.1, 2.2, 2.3. Each of these calculated correlations comprises the information of the chromatogram of the respective separation column 2.1, 2.2, 2.3.

For a precise determination of the chromatograms of the separation columns 2.1, 2.2, 2.3, the modulation functions with which the parts of the sample are modulated when being inserted in the separation columns 2.1, 2.2, 2.3 have certain characteristics. In the following, the characteristics of the modulation functions employed in the apparatus 1 shown in FIG. 1 and the method illustrated with the flowchart diagram in FIG. 2 are explained.

Figure 3:
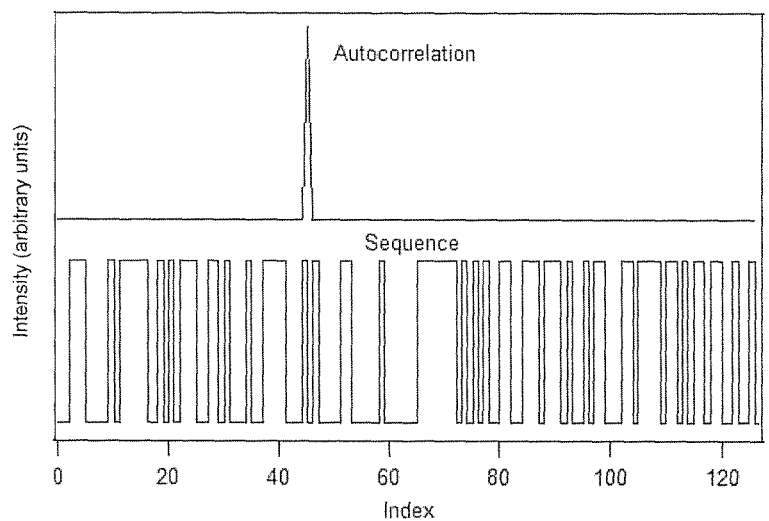

FIG. 3 shows one of the modulation functions employed in the apparatus 1 and the method, the modulation function being denoted as "sequence", together with its autocorrelation. In this figure, the x-axis is an index which corresponds to the numbering of time units of the modulation function and its autocorrelation, while the y-axis is the intensity of the modulation function and its autocorrelation, respectively. The width of the time units can be chosen to have any number or fraction of seconds such that the length in time of the modulation function can be adapted to the specific needs of the measurement.

As can be seen in FIG. 3, the autocorrelation is a two-valued function having a single peak. Thus, when calculating the correlation between the signal measured with the detector 4 and the respective modulation function, the chromatogram of the part of the sample which has been properly modulated with the respective modulation function and has passed the respective separation column 2.1, 2.2, 2.3 is included in the correlation.

As further characteristic, the employed modulation functions all have a same length which corresponds to the number of employed separation columns 2.1, 2.2, 2.3 times the time the investigated sample needs to pass the slowest of the employed separation columns 2.1, 2.2, 2.3. Thus, depending on whether two or three of the separation columns 2.1, 2.2, 2.3 of the apparatus 1 shown in FIG. 1 are employed, the length of the modulation functions is two or three times the time the investigated sample needs to pass the slowest of the employed separation columns 2.1, 2.2, 2.3.

Figure 4:
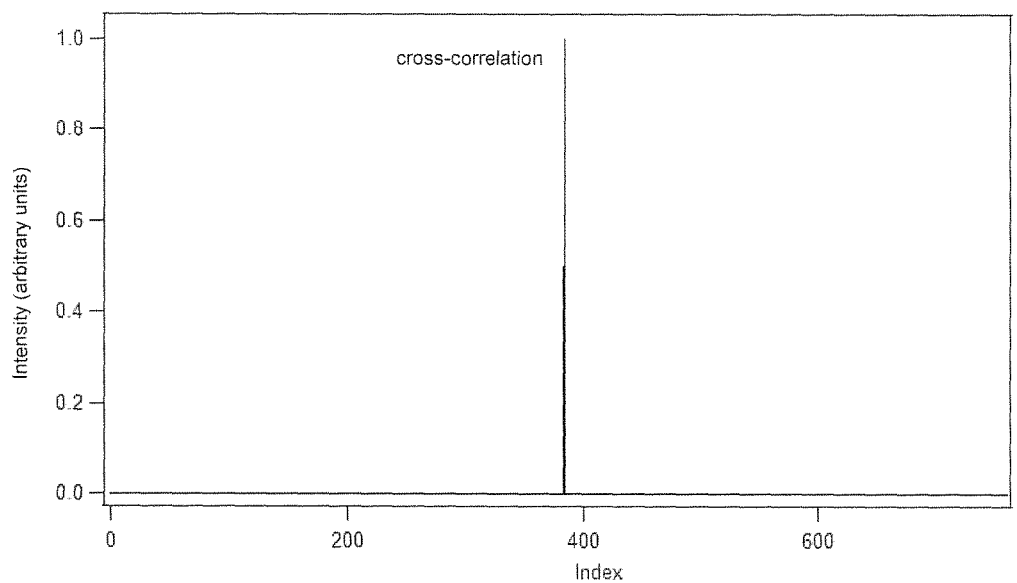

As illustrated in FIG. 4, the employed modulation functions additionally have the characteristic that each pair of two modulation functions chosen from the employed modulation functions has a cross-correlation which is a two-valued function having a single peak. The position of this single peak in the cross-correlation is at a distance from an end of the cross-correlation. This distance is an integer number times the length of the cross-correlation divided by the number of employed separation columns 2.1, 2.2, 2.3, wherein the integer number is larger than zero and smaller than the number of employed separation columns 2.1, 2.2, 2.3. In the illustration shown in FIG. 4, the single peak is positioned in the centre of the cross-correlation because there are only two separation columns 2.1, 2.2, 2.3 employed. If there would be three separation columns 2.1, 2.2, 2.3 employed, the single peak in the cross-correlation would be either positioned at one third or two third of the cross-correlation.

The effect of the single peak in the cross-correlations of the pairs of two modulation functions is that a correlation calculated from the signal measured with the detector 4 and a first one of a pair of two modulation functions comprises as well the information of the chromatogram of the separation column 2.1, 2.2, 2.3 where the corresponding part of the sample is inserted modulated with the second one of the pair of two modulation functions. Thus, the calculated correlation comprises the information of the chromatograms of both the separation columns 2.1, 2.2, 2.3 where the corresponding parts of the sample are inserted modulated with the two modulation functions. However, the information of the first chromatogram which belongs to the separation column 2.1, 2.2, 2.3 where the corresponding part of the sample is inserted modulated with the first one of the two modulation functions is located in the beginning of the cross-correlation, while the information of the second chromatogram which belongs to the separation column 2.1, 2.2, 2.3 where the corresponding part of the sample is inserted modulated with the second one of the two modulation functions may be located somewhere else. More precisely, the location of the second chromatogram's information in the correlation depends on the position of the single peak in the cross-correlation of the pair of two modulation functions.

In the apparatus 1 shown in FIG. 1 and in the method illustrated in FIG. 2, the second chromatogram's information is located behind the information of the first chromatogram in the correlation between the signal measured with the detector 4 and the first modulation function. One reason for this position is that the employed modulation functions have a length of the number of employed separation columns 2.1, 2.2, 2.3 times the time the investigated sample needs to pass the slowest of the employed separation columns 2.1, 2.2, 2.3. The other reason is that the position of the single peak in the cross-correlation is at a distance of an integer number times the length of the cross-correlation divided by the number of employed separation columns 2.1, 2.2, 2.3 from an end of the cross-correlation, wherein the integer number is larger than zero and smaller than the number of employed separation columns 2.1, 2.2, 2.3.

This positioning of the first and the second chromatogram applies to all possible pairs of two modulation functions chosen from the employed modulation functions. Thus, the first chromatogram is always located in the beginning of the correlation calculated for the respective first modulation function, while the information of the other chromatograms are always located further back in the correlation. Consequently, if the correlation is calculated between the signal measured with the detector 4 and one of the modulation functions, the chromatogram belonging to the separation column 2.1, 2.2, 2.3 where the corresponding part of the sample is inserted modulated with the respective modulation function can be obtained by cutting off the first part of the calculated correlation.

In the following, this positioning of the chromatograms in the calculated correlations is illustrated in an example where two separation columns are employed.

Figure 5:
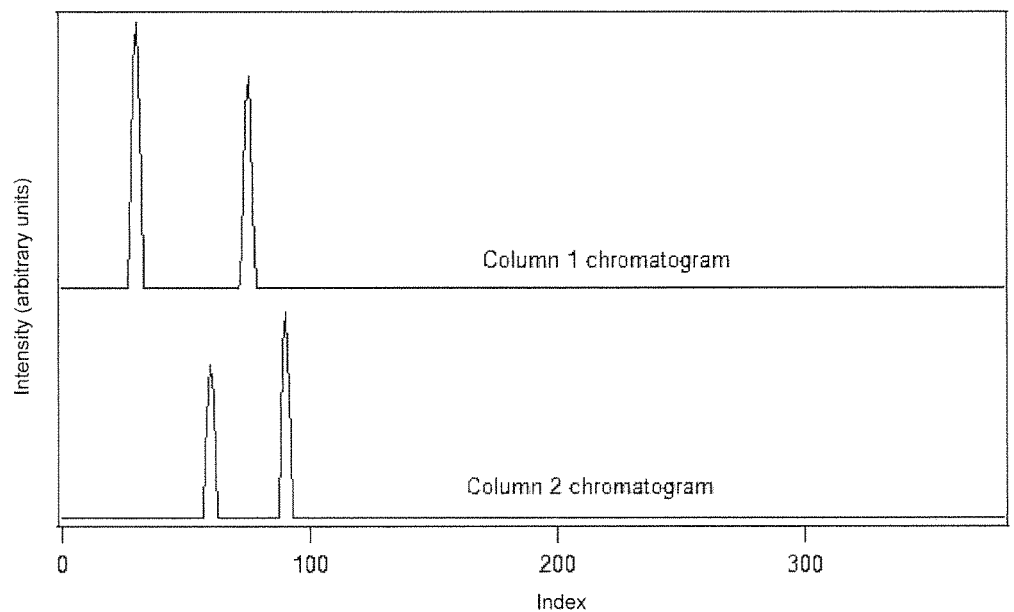

FIG. 5 shows the chromatograms of two different separation columns 2.1, 2.2. Both chromatograms have a length of 400 time units and comprise two peaks. Therefore, in both separation columns 2.1, 2.2, the respective part of the sample is separated in two constituent parts which take different times to pass the corresponding separation column 2.1, 2.2. When performing a measurement, the two parts of the sample are both modulated with a modulation function having a length of 800 time units when being inserted in the respective separation column 2.1, 2.2. These two modulation functions have each an autocorrelation which is a two-valued function and which has one single peak. Furthermore, the cross-correlation of the two modulation functions is a two-valued function with one single peak in the centre like the cross-correlation shown in FIG. 4.

Figure 6:
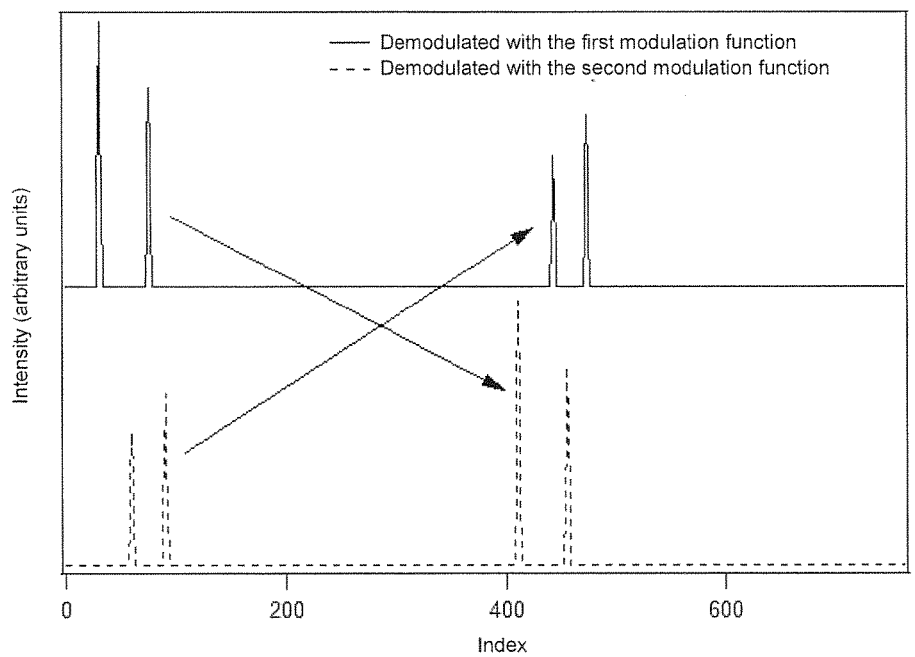

The correlations calculated between the signal measured with the detector 4 and both modulation functions are shown in FIG. 6. As can be seen, the first half of both correlations corresponds to the respective chromatogram. At the same time, as indicated by the arrows, the second half of the correlations corresponds to the respective other chromatogram.

The invention is not limited to the embodiment shown above. The apparatus may for example comprise only two, four, five or even more than five separation columns. Depending on the number of separation columns of the apparatus, more than two or three separation columns may be employed in the method.

The modulation functions which are employed are not limited to the ones having the specific characteristics described in the above embodiment. For example, it is not required that they each have an autocorrelation which is a two-valued function with one single peak. Some or all of them may have an autocorrelation with one single peak which is not a two-valued function. In this case, on both sides of the single peak, the autocorrelation may have a constant value or may have low sidebands. Similarly, it is not required that each pair of two modulation functions chosen from the employed modulation functions has a cross-correlation which is a two-valued function having one single peak. Some or all of the cross-correlations may have one single peak without being a two-valued function. In this case, the cross-correlations may have low or constant sidebands on both sides of the single peak. Furthermore, the peak positions of the single peaks in the cross-correlations may differ from the peak positions in the embodiment explained above. For example, the peak positions may be in the vicinity of one of the ends of the respective cross-correlation. But other peak positions are possible as well.

In even another variation, some or all of the cross-correlations may have no peak but have a nearly constant value over their entire length.

In summary, it is to be noted that a method and an apparatus pertaining to the technical field initially mentioned are provided which enable obtaining a full chromatogram comprising the information of the chromatograms of more than one separation column more quickly while maintaining the signal to noise ratio in the chromatograms.

The invention claimed is:
1. A method for determining a chromatogram, including:
a) a first step where a sample is inserted in two separation columns, wherein for each separation column, a corresponding part of the sample is inserted in the respective separation column with a corresponding insertion device which is controlled by a corresponding modulation function for generating a corresponding modulated part of the sample in the respective separation column when the respective part of the sample is inserted in the respective separation column, wherein the modulation functions with which the parts of the sample are modulated in the separation columns when the parts of the sample are inserted in the separation columns differ from each other,
b) a second step where each modulated part of the sample is guided through the respective separation column,
c) a third step where a signal of each modulated part of the sample is measured with a same detector after having passed the respective separation column, and
d) a fourth step where for each separation column, a correlation of the signal and the modulation function with which the corresponding part of the sample is modulated in the respective separation column when being inserted in the respective separation column is calculated in order to determine the chromatogram of the respective separation column.
2. The method according to claim 1, wherein
a) in the first step, the sample is inserted in three, four, five or more separation columns, wherein for each separation column a corresponding part of the sample is inserted in the respective separation column with a corresponding insertion device which is controlled by a corresponding modulation function for generating a corresponding modulated part of the sample in the respective separation column, wherein the modulation functions with which the parts of the sample are modulated in the separation columns differ from each other, wherein b) in the second step, each modulated part of the sample is guided through the respective separation column, wherein
c) in the third step, the signal of each modulated part of the sample is measured with the same detector after having passed the respective separation column, and wherein
d) in the fourth step, for each separation column, a correlation of the signal and the modulation function with which the corresponding part of the sample is modulated in the respective separation column is calculated in order to determine the chromatogram of the respective separation column.
3. Method according to claim 1, characterised in that an autocorrelation of at least one of the modulation functions is a two-valued function.
4. Method according to claim 1, characterised in that the autocorrelation of each of the modulation functions is a two-valued function.
5. Method according to claim 1, characterised in that the modulation functions have a same length.
6. Method according to claim 5, characterised in that the length of the modulation functions is at least the number of separation columns times the time the sample requires to pass the separation column that is passed the slowest by the sample.
7. Method according to claim 1, characterised in that a cross-correlation of two modulation functions chosen from the modulation functions is a function with a single peak at a peak position.
8. Method according to claim 7, characterised in that the cross-correlation of each pair of two modulation functions chosen from the modulation functions is a function with a single peak at a peak position.
9. Method according to claim 7, characterised in that the cross-correlation of the respective two modulation functions is a two-valued function with a single peak at a peak position.
10. Method according to claim 7, characterised in that the peak position is located in the cross-correlation in a region with a length of 1%, 2%, 5%, 10% or 20% of the cross-correlation's length, the region's centre being located at a distance from an end of the cross-correlation, the distance being an integer multiplied with the length of the cross-correlation divided by the number of employed separation columns.
11. Method according to claim 1, characterised in that the method is for determining a liquid chromatogram.
12. Method according to claim 1, characterised in that the method is for determining a gas chromatogram.
13. Method according to claim 1, characterised in that the detector is a mass spectrometer.
14. Apparatus for determining a chromatogram according to claim 1, comprising:
a) at least two separation columns,
b) for each separation column an inserting device for inserting a part of a sample into the respective separation column, the inserting devices each being controlled by a corresponding modulation function for generating a corresponding modulated part of the sample in the respective separation column when the respective part of the sample is inserted in the respective separation column, wherein the modulation functions with which the parts of the sample are modulatable in the separation columns when the parts of the sample are inserted in the separation columns differ from each other, c) a detector for measuring a signal of the modulated parts of the sample after having passed the respective separation column, and d) a calculation unit for calculating for each separation column the correlation of the signal with the modulation function with which the part of the sample which is inserted into the respective separation column is modulated when being inserted in the respective separation column in order to determine the chromatograms of the separation columns.

15. Method according to claim 1, wherein an autocorrelation of at least one of the modulation functions is a function with one single peak and low sidebands.

16. Apparatus according to claim 14, wherein an autocorrelation of at least one of the modulation functions is a function with one single peak and low sidebands.

* * * * *